United States Patent
Kuo

(10) Patent No.: US 10,512,524 B2
(45) Date of Patent: Dec. 24, 2019

(54) METHOD AND SYSTEM FOR DENTAL VISUALIZATION

(71) Applicant: Align Technology, Inc., San Jose, CA (US)

(72) Inventor: Eric Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/496,996

(22) Filed: Apr. 25, 2017

(65) Prior Publication Data

US 2017/0224442 A1    Aug. 10, 2017

Related U.S. Application Data

(63) Continuation of application No. 12/346,719, filed on Dec. 30, 2008, now Pat. No. 9,642,678.

(51) Int. Cl.
| | |
|---|---|
| *G06G 7/48* | (2006.01) |
| *A61C 7/00* | (2006.01) |
| *G06F 17/50* | (2006.01) |
| *A61C 7/08* | (2006.01) |

(52) U.S. Cl.
CPC ............... *A61C 7/002* (2013.01); *A61C 7/08* (2013.01); *G06F 17/5009* (2013.01); *A61C 2007/004* (2013.01)

(58) Field of Classification Search
None
See application file for complete search history.

(56) References Cited

U.S. PATENT DOCUMENTS

| | | | |
|---|---|---|---|
| 2,467,432 | A | 4/1949 | Kesling et al. |
| 3,407,500 | A | 10/1968 | Kesling et al. |
| 3,600,808 | A | 8/1971 | Reeve et al. |
| 3,660,900 | A | 5/1972 | Andrews et al. |
| 3,683,502 | A | 8/1972 | Wallshein et al. |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

Rodrigues, Maria Andreia F. et al., "An Interactive Simulation System for Training and Treatment Planning in Orthodontics", Apr. 15, 2007, Computers & Graphics 31, Elsevier Ltd. (Year: 2007).*

(Continued)

*Primary Examiner* — Cedric Johnson
(74) *Attorney, Agent, or Firm* — Wilson Sonsini Goodrich & Rosati

(57) ABSTRACT

In particular embodiments, method, apparatus and system for receiving digital representations of the initial parameters of a dentition; simulating a first orthodontic treatment process on the digital representations of the initial parameters, displaying a set of output results from the simulation of the first orthodontic treatment process, simulating a second orthodontic treatment process on the output results from the simulation of the first orthodontic treatment process, and displaying a set of output results from the simulation of the second orthodontic treatment process are provided.

20 Claims, 12 Drawing Sheets

(56) References Cited

U.S. PATENT DOCUMENTS

| | | |
|---|---|---|
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra |
| 4,936,862 A | 6/1990 | Walker et al. |
| 4,937,928 A | 7/1990 | Van et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen et al. |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary et al. |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,482,298 B1 | 11/2002 | Bhatnagar et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,688,885 B1 | 2/2004 | Sachdeva et al. |
| 6,705,863 B2 | 3/2004 | Phan et al. |
| 6,722,880 B2 | 4/2004 | Chishti et al. |
| 6,733,289 B2 | 5/2004 | Manemann et al. |
| 7,074,038 B1 | 7/2006 | Miller |
| 7,306,152 B2 | 12/2007 | Culp et al. |
| 7,930,189 B2 | 4/2011 | Kuo |
| 7,987,099 B2 | 7/2011 | Kuo et al. |
| 9,642,678 B2 | 5/2017 | Kuo |
| 2002/0006597 A1 | 1/2002 | Andreiko et al. |

(56) References Cited

U.S. PATENT DOCUMENTS

| | | | |
|---|---|---|---|
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer et al. |
| 2004/0013993 | A1 | 1/2004 | Ito |
| 2004/0015327 | A1* | 1/2004 | Sachdeva ............... A61C 7/00 702/167 |
| 2004/0128010 | A1 | 7/2004 | Pavlovskaia et al. |
| 2005/0038669 | A1 | 2/2005 | Sachdeva et al. |
| 2005/0055118 | A1 | 3/2005 | Nikolskiy et al. |
| 2005/0192835 | A1 | 9/2005 | Kuo et al. |
| 2007/0129991 | A1* | 6/2007 | Kuo .................... A61C 7/00 705/2 |
| 2007/0168152 | A1* | 7/2007 | Matov ................. A61C 7/00 702/155 |
| 2009/0191502 | A1 | 7/2009 | Cao et al. |
| 2009/0246726 | A1 | 10/2009 | Chelnokov et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Boyd, Robert L. et al., "Three Dimensional Diagnosis and Orthodontic Treatment of Complex Malocclusions with the Invisalign Appliance", Dec. 2001, Seminars in Orthodontics, vol. 7, No. 4. (Year: 2001).*

Doyle, Audrey, "Digital Dentistry", Oct. 2000, Computer Graphics World. (Year: 2000).*

Alcaniz, "An Advanced System for the Simulation and Planning of Orthodontic Treatment", Medical Image Analysis, vol. 2, No. 1, 1998, 61-77.

Li, et al., "Orthodontic Simulation and Diagnosis: An Enhanced Tool for Dentists", IEEE Engineering in Medicine and Biology, 27th Annual Conference, Sep. 1-4, 2005, 4345-4348.

Rodrigues, et al., "An Interactive Simulation System for Training and Treatment Planning in Orthodontics", Computers and Graphics 31, 2007, 688-697.

Sarver, et al., "Dynamic Smile Visulaization and Quantification: Part 2. Smile Analysis and Treatment Strategies", American Association of Orthodontists, 2003, 116-127.

AADR. American Association for Dental Research, Summary of Activities, Mar. 20-23, 1980, Los Angeles, CA, p. 195.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures,"IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy. swin.edu.au/-pbourke/prolection/coords>.

Boyd et al., "Three Dimensional Diagnosis and Orthodontic Treatment of Complex Malocclusions With the lnvisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on The Uses of the Computer in Orthodontic Practice (Part 1)," J. Clin. Orthod., 13(7):442-453 (Jul. 1979).

(56) References Cited

OTHER PUBLICATIONS

Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com pg. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClear™ product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . .>.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre-and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.

(56) References Cited

OTHER PUBLICATIONS

Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003, 114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.

(56) References Cited

OTHER PUBLICATIONS

U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268, 1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances-Pro Lab product information for patients, 2 pages (2002).

\* cited by examiner

METHOD AND SYSTEM FOR DENTAL VISUALIZATION

RELATED APPLICATION SECTION

This application is a continuation of, and claims priority to, U.S. patent application Ser. No. 12/346,719, filed Dec. 30, 2008, now U.S. Pat. No. 9,642,678, issued May 9, 2017, entitled "METHOD AND SYSTEM FOR DENTAL VISUALIZATION" by Eric Kuo, and assigned to the assignee of the present application.

BACKGROUND

The present disclosure relates generally to the field of dentistry. More specifically, the present disclosure relates to the field of virtual orthodontic treatment planning and visualization.

One main objective of orthodontics is to move a patient's teeth into an optimal target occlusion, or a position in which the teeth function optimally and are aesthetically pleasing to the patient. Conventionally, appliances such as braces, which are a bracket and arch wire system, are applied to the teeth of the patient by an orthodontist or other qualified dental professional. The brackets in the braces system are mounted on the surface of the teeth of a patient and the arch wire couples all the brackets on the same jaw to one another. The arch wire is incrementally tightened over time during office visits to the treating professional, exerting a continual force on the teeth, gradually moving them toward a desired target position.

Recently, a system for treating dental malocculsions has become available under the trade name Invisalign® System. The Invisalign® System has two components. The first component is called ClinCheck® and allows practitioners to simulate treatment of teeth by observing and modeling two-week stages of tooth movement. Based on the results of the ClinCheck® component, the second component comprises aligners which are thin, clear, plastic removable dental appliances that correspond to each treatment stage of the ClinCheck® simulation. The aligners are manufactured using advanced computer-controlled fabrication systems. Each aligner is worn by the patient for approximately two weeks before it is exchanged for a next stage aligner intended to further reposition the teeth. The Invisalign® System addresses many of the significant limitations of conventional braces. In particular, the Invisalign® System aligners are virtually invisible, and are therefore more ascetically pleasing for the patient. Second, the aligners are generally less painful and uncomfortable than are traditional braces. Additionally, the aligners can be removed to permit conventional oral hygiene, thus being more healthy for the patient's teeth.

SUMMARY

Embodiments of the present disclosure in one aspect includes receiving digital representations of the initial parameters of a dentition, simulating a first orthodontic treatment process on the digital representations of the initial parameters, displaying a set of output results from the simulation of the first orthodontic treatment process, simulating a second orthodontic treatment process on the output results from the simulation of the first orthodontic treatment process, and displaying a set of output results from the simulation of the second orthodontic treatment process.

A computer program product in another aspect includes a medium readable by a computer, the computer readable medium having computer program code adapted to receive digital representations of the initial parameters of a dentition, simulate a first orthodontic treatment process on the digital representations of the initial parameters, display a set of output results from the simulation of the first orthodontic treatment process, simulate a second orthodontic treatment process on the output results from the simulation of the first orthodontic treatment process, and display a set of output results from the simulation of the second orthodontic treatment process.

DETAILED DESCRIPTION

Figure 1A:
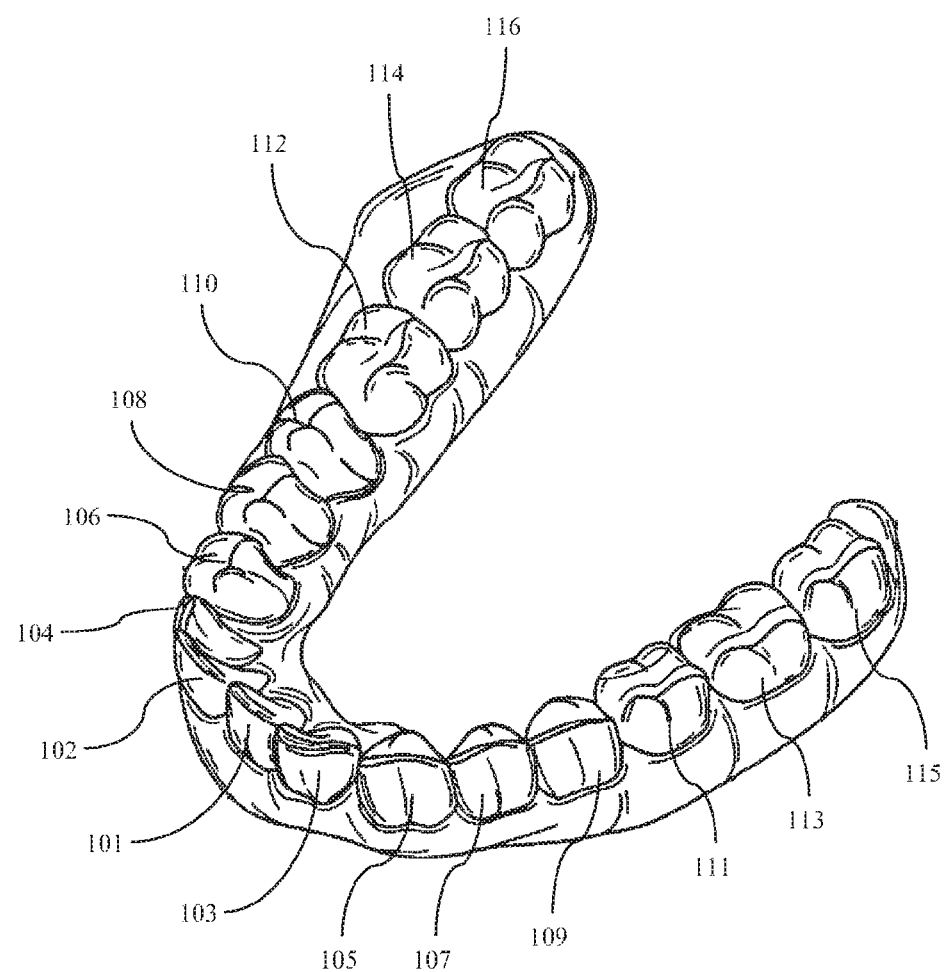
FIG. 1A is a diagram of the lower jaw and teeth of a patient's mouth.

FIG. 1A is a diagram of the lower jaw and teeth of a patient's mouth. Referring to FIG. 1A, the lower jaw 100 of a patient may include teeth such as the left central incisor 101, the right central incisor 102, the left lateral incisor 103, the right lateral incisor 104, the left cuspid or canine 105, the right cuspid 106, the left first bicuspid 107, the right first bicuspid 108, the left second bicuspid 109, the right second bicuspid 110, the left first molar 111, the right first molar 112, the left second molar 113, the right second molar 114, the left third molar or wisdom tooth 115, and the right third molar or wisdom tooth 116. The upper jaw of a patient may have a similar set of incisors, cuspids, bicuspids, and molars. The relationship between the individual teeth of the jaw 100 and the relationship between the sets of teeth on the upper and lower jaws 100 are used to determine the corrective measures needed in a chosen orthodontic procedure. Different types of malocclusion, a non-optimal positioning of a patient's teeth, may include, among others, overbite, also known as class 11 malocclusion, underbite, also known as class III malocclusion, overjet, and diastema. Individual teeth position may also affect the type of chosen orthodontic procedure, such as crooked or rotated teeth.

Figure 1B:
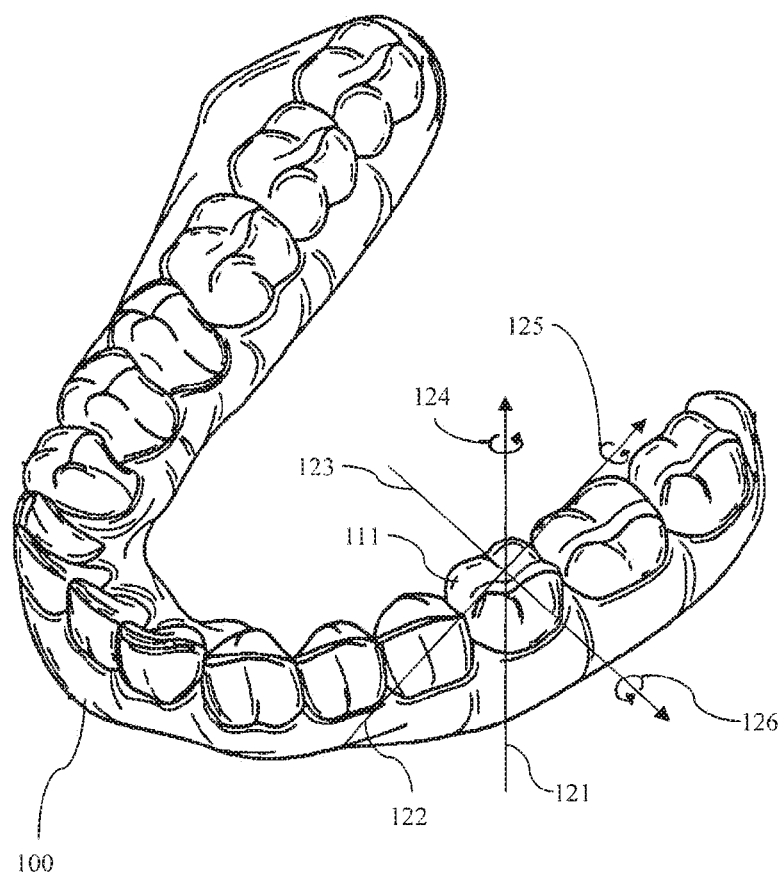
FIG. 1B illustrates a patient's jaw and provides a general indication of how teeth may be moved.
Figure 1C:
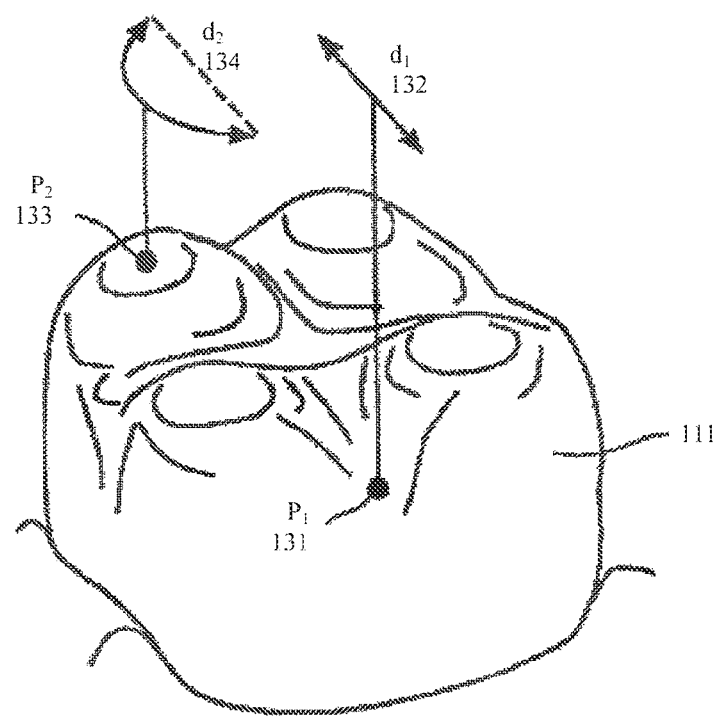
FIG. 1C illustrates a single tooth and illustrates how tooth movement distances may be determined.

FIG. 1B illustrates a patient's jaw and provides a general indication of how teeth may be moved and FIG. 1C illustrates a single tooth and illustrates how tooth movement distances may be determined. Referring to FIG. 1B, a representative jaw 100 includes a plurality of teeth. To understand how the teeth may be moved, an arbitrary centerline 121 is drawn through one of the teeth 111. With reference to this centerline, the tooth may be moved in the orthogonal direction represented by axes 121-123, where 121 represents the centerline. Additionally, the tooth may be moved about the axes 121-123 as indicated by 124-126. Thus, all possible free-form motions of the tooth may be performed.

Referring now to FIG. 1C, the magnitude of any tooth movement achieved by methods and systems, may be defined in terms of the maximum linear translation of any point Pi on a tooth 111. Each point Pi will undergo a cumulative translation as that tooth is moved in any of the orthogonal or rotational directions defined in FIG. 1B. That is, while the point will usually follow a non-linear path, there will be a linear distance between any point in the tooth when determined at any two times during the treatment. Thus an arbitrary point P1 131 may in fact undergo a true side-to-side translation as indicated by arrow d1 132, while a second arbitrary point P2 133 may travel along an arcuate path, resulting in a target translation d2 134.

There are a number of methods of correcting malocclusion, or the poor or non-optimal positioning of the teeth of a patient. Such methods include, but are not limited to, oral surgery, elastics, removable appliances, such as polymeric shell aligners and palate expanders, and fixed orthodontic appliances, such as braces. While each method may be used individually, in some cases it may be desirable for the patient and treating dental or orthodontic professional to use a combination of two or more of the same or different aforementioned methods. Possible reasons for using a combination of two or more different treatments may be, for example, for optimizing treatment for patient comfort, time requirements, monetary cost, or optimal target result.

Figure 2:
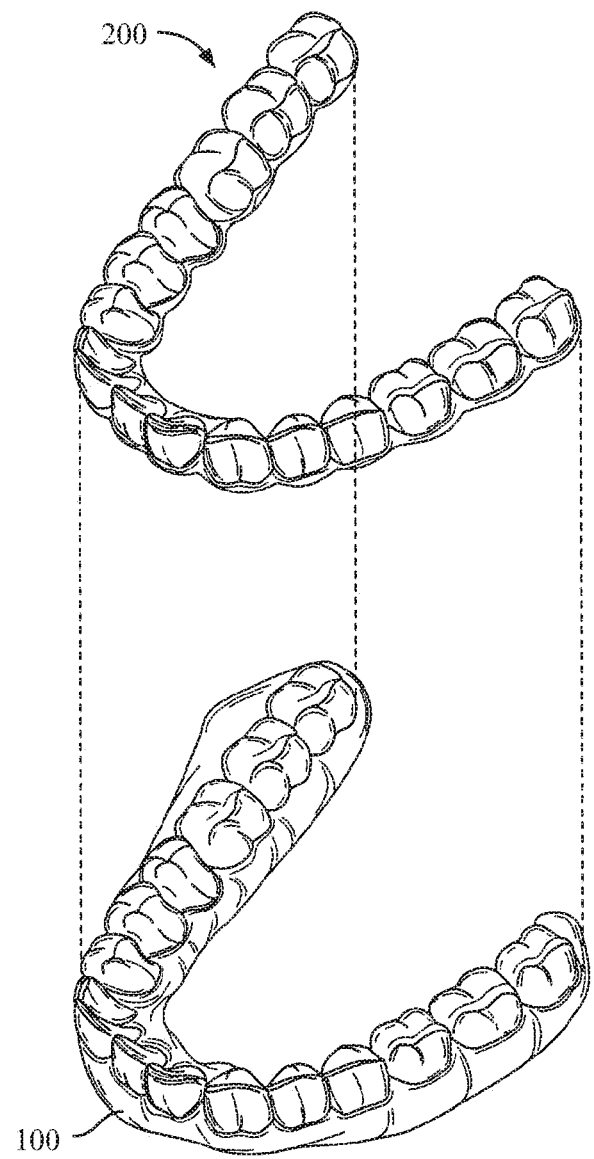
FIG. 2 illustrates an example of a non-bracket polymeric shell aligner for use in one or more embodiments of the present disclosure.

FIG. 2 illustrates an example of a non-bracket polymeric shell aligner for use in one or more embodiments of the present disclosure. Referring to FIG. 2, systems according to one or more embodiments of the present disclosure may comprise a plurality of incremental position adjustment appliances. The appliances are intended to effect incremental repositioning of individual teeth in the jaw as described generally above. A preferred appliance 200 will comprise a polymeric shell having a cavity shaped to receive and resiliently reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously.

Referring still to FIG. 2, the polymeric appliance 200 is shaped to fit over the teeth of the jaw 100 and is preferably formed from a thin sheet of a suitable elastomeric polymeric, such as Tru-Tain 0.03 in. thermal forming dental material, Tru-Tain Plastics, Rochester, Minn. 55902. Usually, no wires or other means will be provided for holding the appliance in place over the teeth. In some cases, however, it will be desirable or necessary to provide individual anchors on teeth with corresponding receptacles or apertures in the appliance 200 so that the appliance can apply an upward or other force or torque on the tooth which would not be feasible in the absence of such an anchor.

Figure 3:
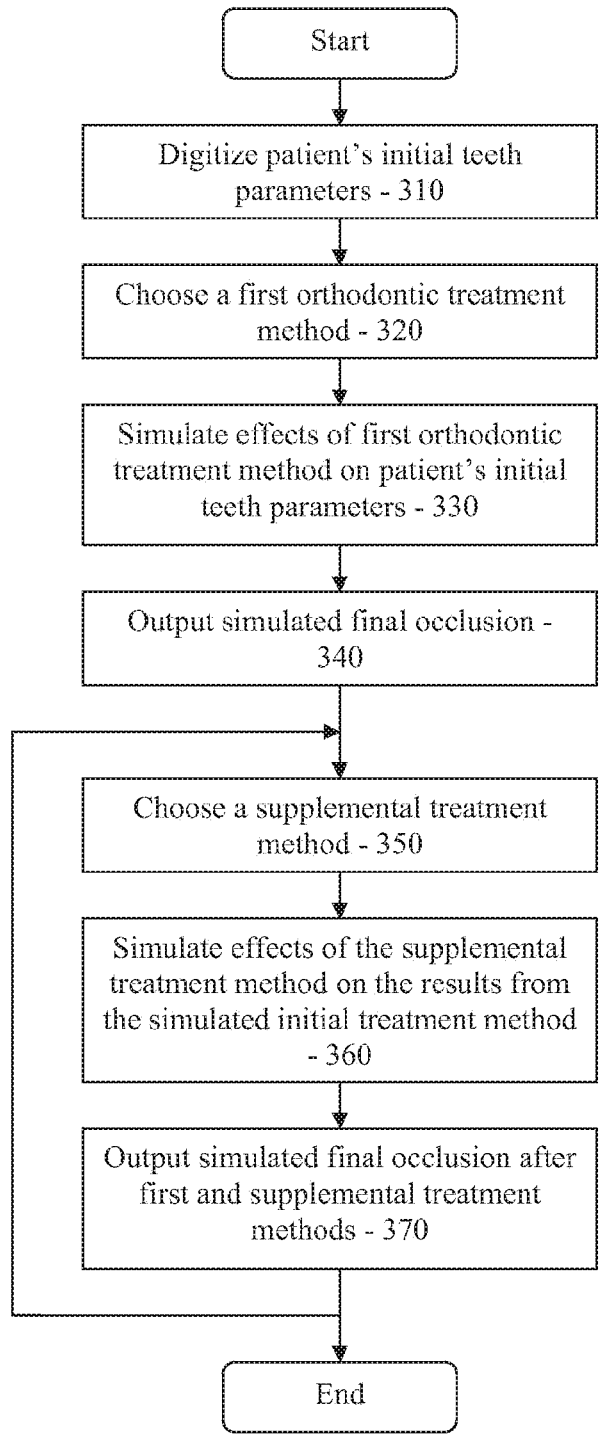
FIG. 3 illustrates a procedure for providing orthodontic treatment based on one or more treatments in one aspect.

FIG. 3 illustrates a method of treating a patient using one or more orthodontic treatments. Referring to FIG. 3, a flow chart of a method of treating a patient using one or more orthodontic treatments is shown. In one embodiment of the present disclosure, it may be advantageous to simulate the effects of a chosen method or methods of treating the malocclusion of a patient's teeth. Virtual orthodontics is a useful tool for such a simulation. Virtual orthodontics is a method of digitizing patients' initial teeth parameters and applying virtual forces representing the treatment plan on the initial teeth parameters. In one embodiment, the digitization of a patient's initial teeth parameters (310) is done by scanning the teeth and bite set of a patient. This may be done by, among others, interoral scanning, X-ray, or magnetic resonance imaging (MRI). The scan may be a direct scan of the patient's teeth, or an indirect scan, using a dental impression. The digital scan of the patient's initial teeth parameters may include, among others, views of each individual tooth, the position and geometry of each individual tooth, the relationship between neighboring teeth, a view of each individual jaw, and the entire bite set of the patient.

Still referring to FIG. 3, based on the initial tooth parameters, an orthodontist or other dental professional may choose a first treatment method (320) based on, among others, experience, preference, and patient inclination. The preferred first treatment method is the use of polymeric shell appliances, such Align Technology, Inc.'s Invisalign® appliances and those described in U.S. Pat. No. 5,975,893, however other treatment methods may include the use of fixed orthodontic appliances, such as traditional braces, oral surgery, or elastics. The digital representation of the patient's initial teeth parameters is loaded into a software program and the chosen treatment is virtually applied to the digital teeth parameters. The virtual treatment may be a virtual representation of the treatment itself, or may be a geometric representation of the forces that would be applied by the treatment.

A software algorithm is used to simulate the effects of the chosen treatment method on the patient's initial teeth parameters (330). The simulation may output a target occlusion (340), or positioning of the teeth, based on the effects of the chosen first treatment method. The output may be, among others, a visual representation, a mathematical description, or a combination thereof. The output may also display target position and rotation of one or more of, each individual tooth of the patient, the relationship between neighboring teeth, a view of each individual jaw, and the entire bite set of the patient.

A second or supplementary treatment may be chosen by the orthodontist or dental professional (350) to further correct a patient's malocclusion. The supplementary treatment may be a different treatment type than the first treatment, or a further treatment of the same treatment type. A simulation of the supplementary treatment (360) may be done using the output occlusion after the first treatment as the supplementary initial tooth parameters. A virtual representation of the supplementary treatment may be applied to the supplementary initial tooth parameters, and the target output from the application of the supplementary treatment process (370) may be displayed for viewing by the patient and treating professional. If further treatment is still desired or necessary, yet another supplementary treatment may be chosen (350) and simulated (360) and the resulting occlusion outputted (370). This process may be repeated as often as desired until the desired target occlusion may be achieved.

Figure 4:
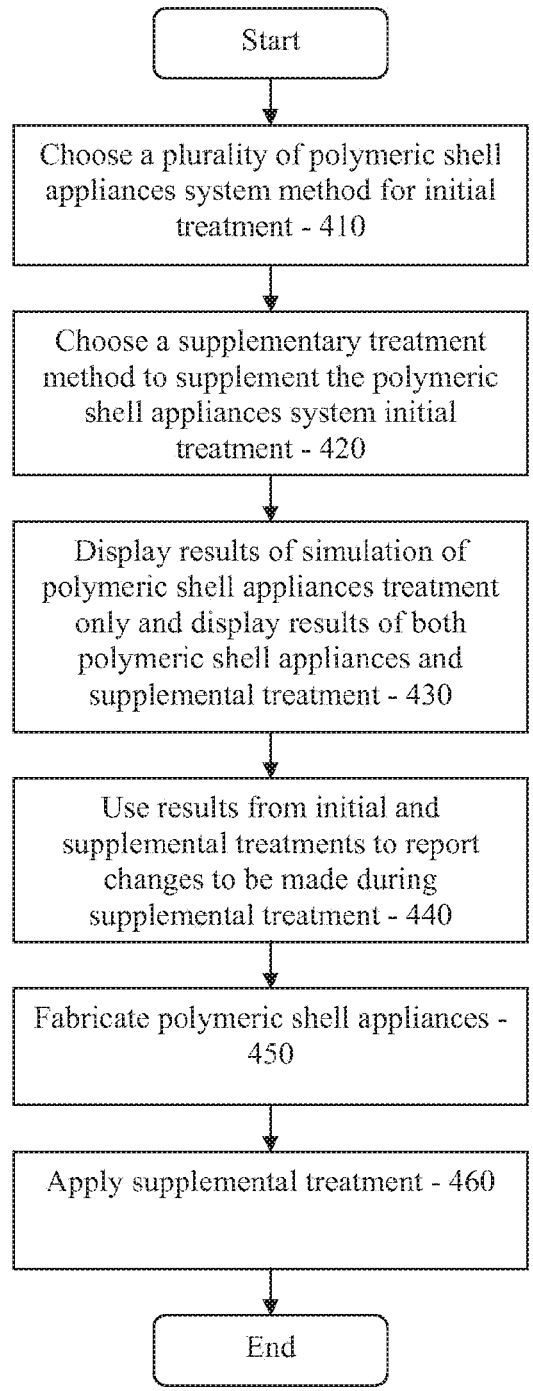
FIG. 4 illustrates a procedure for providing orthodontic treatment based on one or more treatments in another aspect.

FIG. 4 illustrates a method of treating a patient using one or more orthodontic treatments. Referring to FIG. 4, in one embodiment of the present disclosure, the initial chosen orthodontic procedure may include a plurality of polymeric shell aligner appliances (410), such as Align Technology, Inc.'s Invisalign® appliances. The initial orthodontic procedure is shown in FIGS. 5 and 6 of the present disclosure and described in detail below.

Figure 5:
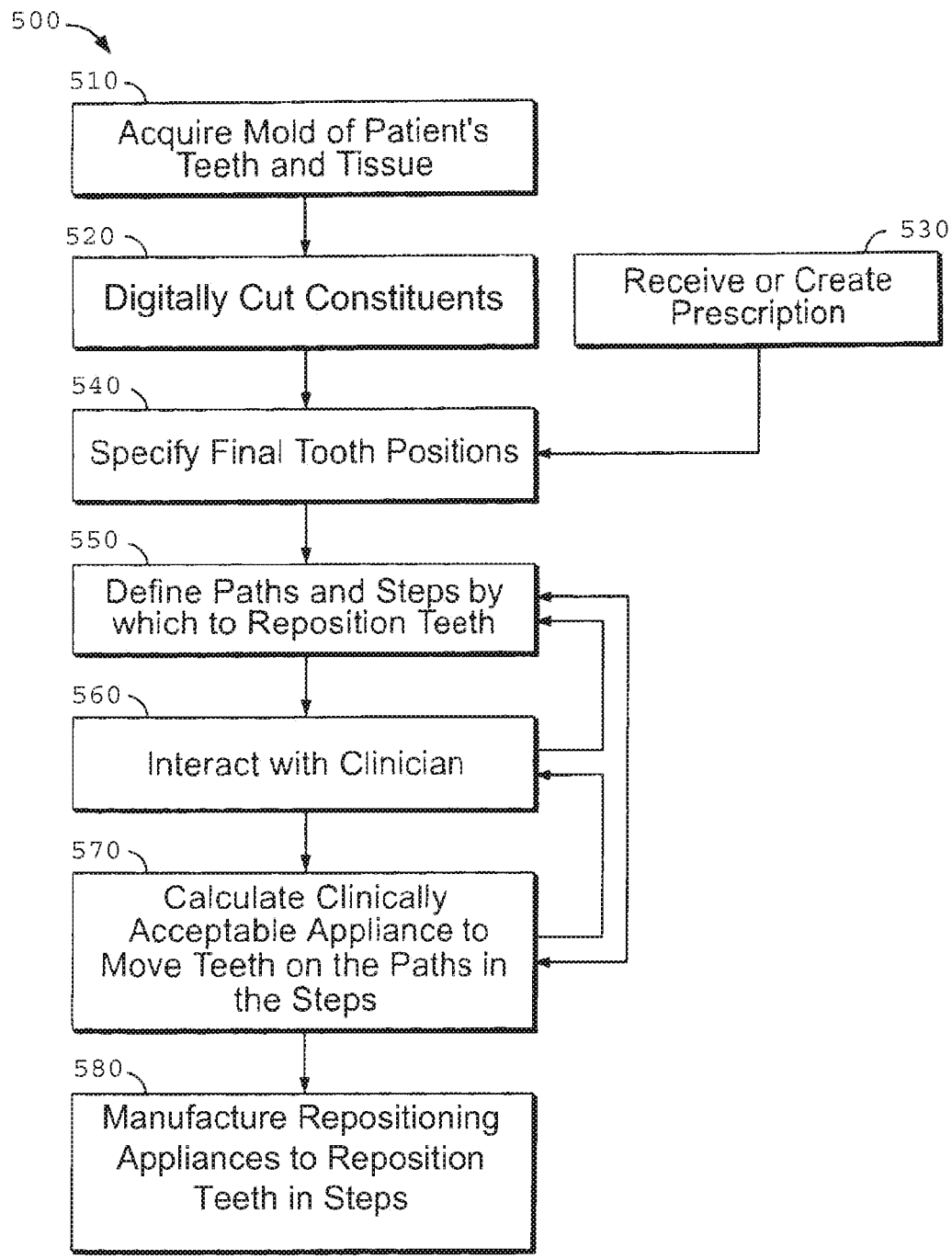
FIG. 5 illustrates an exemplary process for defining and generating repositioning appliances for orthodontic treatment in one aspect.
Figure 6:
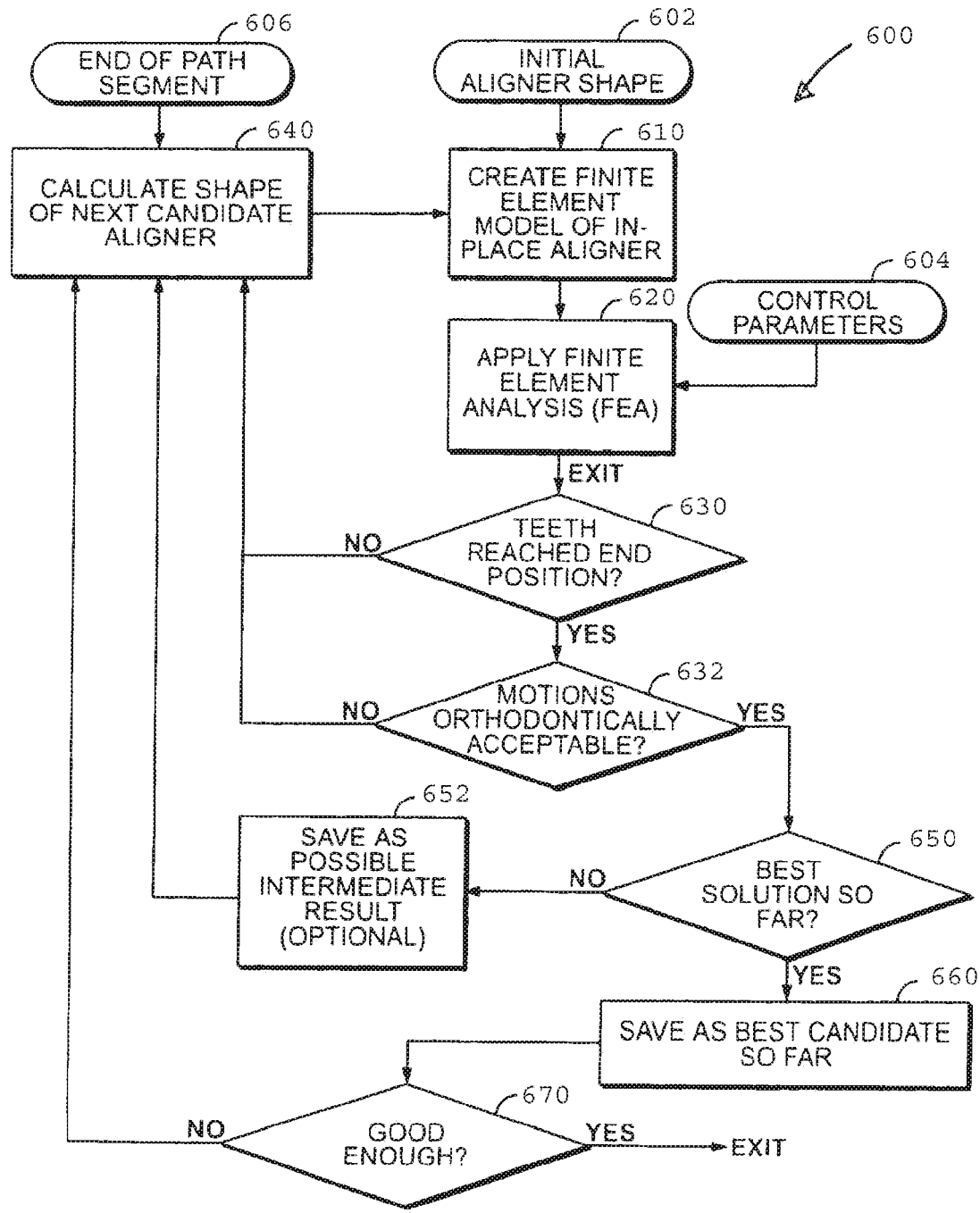
FIG. 6 illustrates a process implementing the appliance calculation of FIG. 5 in one aspect.

FIG. 5 illustrates the general flow of an exemplary process 500 for defining and generating repositioning appliances for orthodontic treatment of a patient. The computational steps of the process are advantageously implemented as computer program modules for execution on one or more conventional digital computers.

As an initial step, a mold or a scan of patient's teeth or mouth tissue is acquired (510). This step generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to digitally cut the tissue constituents from each other (520). In particular, in this step, data structures that digitally represent individual tooth crowns are produced. Advantageously, digital models of entire teeth are produced, including measured or extrapolated hidden surfaces and root structures.

The desired target position of the teeth, that is, the desired and intended end result of orthodontic treatment, can be received from a clinician in the form of a prescription, can be calculated from basic orthodontic principles, or can be extrapolated computationally from a clinical prescription (530). With a specification of the desired target positions of the teeth and a digital representation of the teeth themselves, the target position and surface geometry of each tooth can be specified (540) to form a complete model of the teeth at the desired end of treatment. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a target position for each tooth, the process next defines a tooth path for the motion of each tooth. In one embodiment, the tooth paths are optimized in the aggregate so that the teeth are moved in the quickest fashion with the least amount of round-tripping to bring the teeth from their initial positions to their desired target positions. (Round-tripping is any motion of a tooth in any direction other than directly toward the desired target position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (570), which may determine that at one or more points along one or more tooth paths, the forces that can be generated by the appliance on the then-existing configuration of teeth and tissue is incapable of effecting the repositioning that is represented by one or more tooth path segments. With this information, the subprocess defining segmented paths (550) can recalculate the paths or the affected subpaths.

At various stages of the process, and in particular after the segmented paths have been defined, the process can, and generally will, interact with a clinician responsible for the treatment of the patient (560). Clinician interaction can be implemented using a client process programmed to receive tooth positions and models, as well as path information from a server computer or process in which other steps of process 500 are implemented. The client process is advantageously programmed to allow the clinician to display an animation of the positions and paths and to allow the clinician to reset the target positions of one or more of the teeth and to specify constraints to be applied to the segmented paths. If the clinician makes any such changes, the subprocess of defining segmented paths (550) is performed again.

The segmented tooth paths and associated tooth position data are used to calculate clinically acceptable appliance configurations (or successive changes in appliance configuration) that will move the teeth on the defined treatment path in the steps specified by the path segments (570). Each appliance configuration represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (560). The operation of a process 600 implementing this step is described more fully below.

Having calculated appliance definitions, the process 500 can proceed to the manufacturing step (580) in which appliances defined by the process are manufactured, or electronic or printed information is produced that can be used by a manual or automated process to define appliance configurations or changes to appliance configurations.

FIG. 6 illustrates a process 600 implementing the appliance-calculation step (570) (FIG. 5) for polymeric shell aligners of the kind described in above-mentioned U.S. Pat. No. 5,975,893. Inputs to the process include an initial aligner shape 602, various control parameters 604, and a desired end configuration for the teeth at the end of the current treatment path segment 606. Other inputs include digital models of the teeth in position in the jaw, models of the jaw tissue, and specifications of an initial aligner shape and of the aligner material. Using the input data, the process creates a finite element model of the aligner, teeth and tissue, with the aligner in place on the teeth 610. Next, the process applies a finite element analysis to the composite finite element model of aligner, teeth and tissue 620. The analysis runs until an exit condition is reached, at which time the process evaluates whether the teeth have reached the desired end position for the current path segment, or a position sufficiently close to the desired end position 630. If an acceptable end position is not reached by the teeth, the process calculates a new candidate aligner shape 640. If an acceptable end position is reached, the motions of the teeth calculated by the finite elements analysis are evaluated to determine whether they are orthodontically acceptable 632. If they are not, the process also proceeds to calculate a new candidate aligner shape 640. If the motions are orthodontically acceptable and the teeth have reached an acceptable position, the current aligner shape is compared to the previously calculated aligner shapes. If the current shape is the best solution so far 650, it is saved as the best candidate so far 660. If not, it is saved in an optional step as a possible intermediate result 652. If the current aligner shape is the best candidate so far, the process determines whether it is good enough to be accepted 670. If it is, the process exits. Otherwise, the process continues and calculates another candidate shape 640 for analysis.

The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Mass., the I-DEAS design software products available from Structural Dynamics Research Corporation (SDRC) of Cincinnati, Ohio, and the MSC/NASTRAN product available from MacNeal-Schwendler Corporation of Los Angeles, Calif.

Referring back to FIG. 4, in some instances, correcting certain malocclusions of a patient's bite set and tooth position through the process of the use of the polymeric shell appliance system as described above, may cause the polymeric shell appliance system process to perform at lower than optimal efficiency. In these instances, the polymeric appliance based treatment system may be supplemented with an additional or supplementary orthodontic treatment process (420) occurring before, after or during the polymeric appliance based treatment. One or more of such supplementary treatment processes may include, among others, fixed orthodontic appliance based treatment process, treatments based on using elastics or other removable appliances, or oral surgery, among others.

In one embodiment of the present disclosure, the target tooth position as determined by the routines described in conjunction with FIGS. 5 and 6, may be displayed both separate and in conjunction with the applied results from a simulation of the supplementary orthodontic treatment process (430) (FIG. 4). This allows for the polymeric shell appliances to be manufactured for the treatment of only certain chosen malocclusions of the patient's teeth, while the supplementary treatment is designed to treat the remainder of the corrections. Additionally, this allows the patient and treating dental professional to view the target results from both the polymeric shell appliance system procedure alone, and in conjunction with the selected supplementary treatment process.

Furthermore, the target results from the polymeric shell appliance system treatment process may be used to report what changes may be desired (440) (FIG. 4) in terms of millimeters, degrees, and direction of change as a result of the supplementary treatment process. Given multiple treatment modalities, whether executed, initiated or performed sequentially or concurrently, the target of one treatment mode may be visualized as being independent from the target of the second or another treatment mode, each of which may be analyzed independently with respect to the planned or desired dental or skeletal movement. The combination of these treatments may also be visualized in combination, such that the total movement planned may be computed or determined. Furthermore, adjustments to one treatment mode may be visualized in the combined visualization mode, such that the potential impact of modifications to one treatment mode may be viewed in conjunction with or in view of the combined treatment. In one aspect, alterations to one or more treatment modes may be iterated until, for example, two or more targets may be compatible towards the desired target.

Once the patient and treating professional are satisfied with the results of the simulation as displayed on, for example, a computer display screen, the polymeric shell appliances may be fabricated (450) (FIG. 4) and the supplementary treatment may be applied (460) (FIG. 4). In one aspect, the patient treatment approach described above may include two or more different types of treatments. That is, in one aspect, two or more different orthodontic treatment techniques may be implemented in accordance with embodiments of the present disclosure. Furthermore, in still another aspect, the end or conclusion of one treatment process may coincide or define the beginning or start of another treatment process. That is, with multiple treatment process implemented in conjunction with the various embodiments of the present disclosure, the starting point and end point of each treatment process may be defined by the respective end point or starting point of the subsequent treatment process. For example, in accordance with an orthodontic treatment process which includes two different types of treatments, the beginning of the second treatment type is defined by the end or conclusion of the first treatment type. Moreover, in aspect of the present disclosure, the patient treatment approach may include multiple treatment types that are repeated with equal frequency during the course of the treatment, or alternatively, one or more treatment types repeated more frequently than another one or more treatment types.

Figure 7:
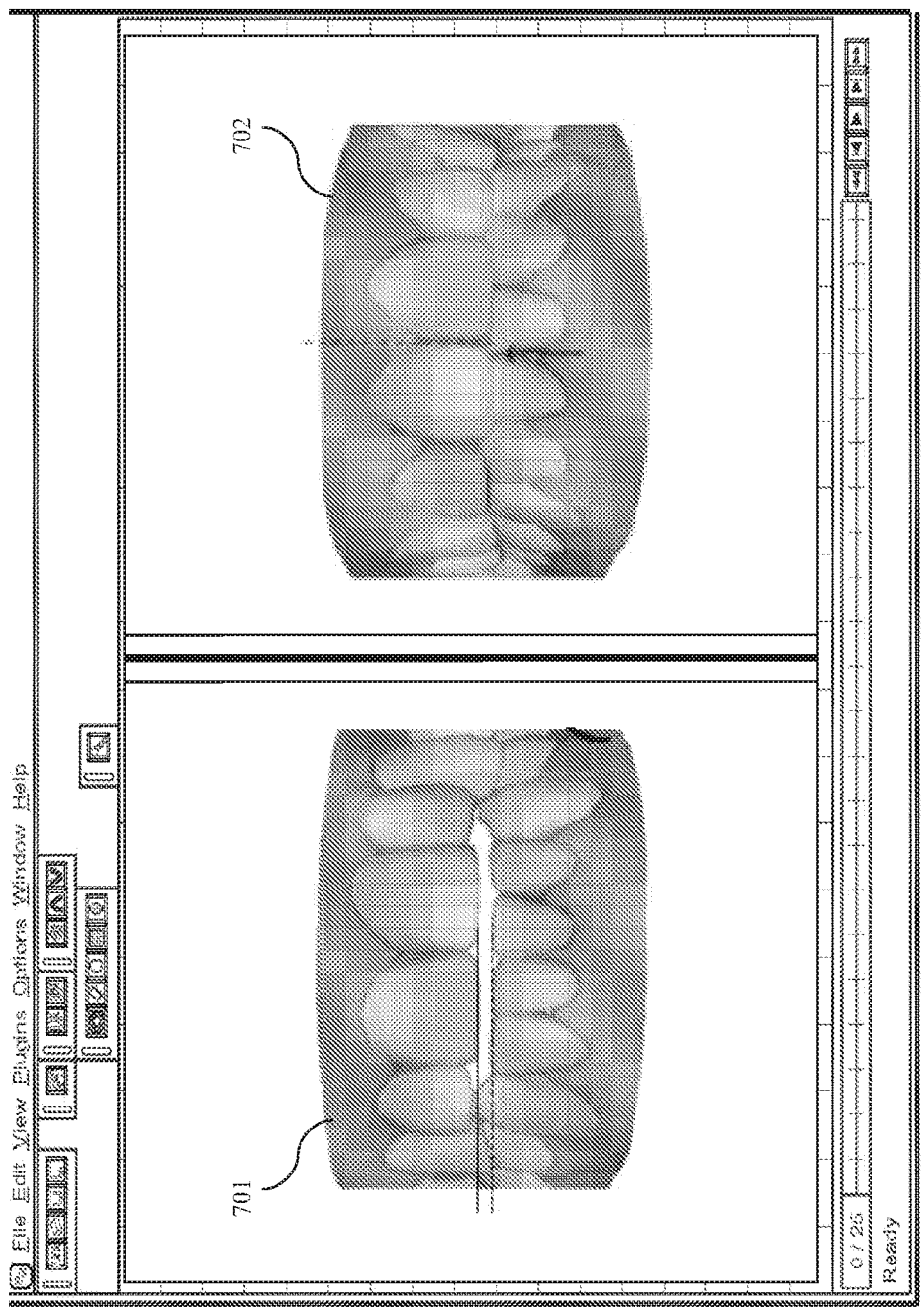
FIG. 7 illustrates simulated output display based on the multiple treatment processes in a further aspect.

FIG. 7 illustrates simulated output display based on the multiple treatment processes in a further aspect. The software program product described in conjunction with FIGS. 4-6 for displaying the simulated output from the polymeric shell appliance system process and the supplementary orthodontic treatment process, may include a multi-screen display. Referring to FIG. 7, the multi-screen display 700 may be used to display the target results from the polymeric shell appliance system procedure alone 701 and the target results from the polymeric shell appliance system procedure in conjunction with the supplementary orthodontic procedure results 702. The side-by-side representation 700 may allow for the patient and treating dental professional to visualize the effects of the supplementary procedure compared to the results from the initial polymeric shell appliance system procedure alone.

Figure 8:
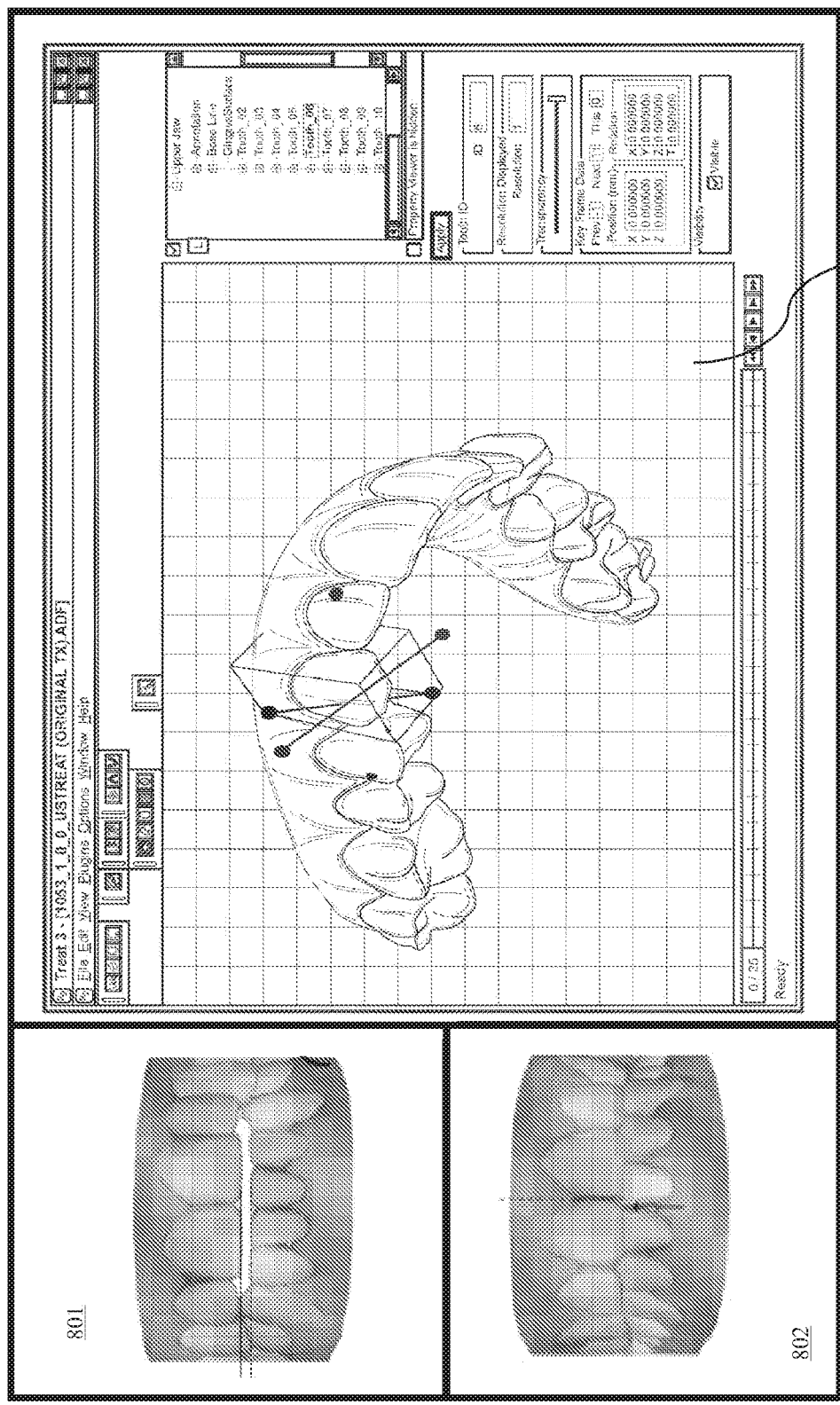
FIG. 8 illustrates a display of an alternate bite relationship viewing window incorporated into the software employed in the processes of FIGS. 4-6 in one aspect.

FIG. 8 illustrates one embodiment of the present disclosure, wherein an alternate bite relationship viewing window is incorporated into the software employed in the processes depicted in FIGS. 4-6. Referring to FIG. 8, one window of the display may be a display of the target result tooth parameters after the polymeric shell appliance system procedure only 801, another window may be of the target result tooth parameters after the polymeric shell appliance system procedure in conjunction with a supplementary orthodontic procedure 802, and a third window may be an editable window, wherein the orthodontist or treating professional may, for example, position the upper or lower or both arches into a new position or change individual tooth positions 803.

A data set including, among others, changes in terms of millimeters, degrees, and direction of change between the target results from the polymeric shell appliance system procedure only as depicted in window 801 compared to the target results from the polymeric shell appliance system in conjunction with a supplementary orthodontic procedure as depicted in window 802, may also be calculated and displayed. This allows for accurate determination of the scope of the surgical or other supplementary procedure to be applied to the patient's teeth. While a three-window display is depicted in FIG. 8, it should be noted that any number of display windows may displayed simultaneously, and each window may be used to display data for any moment in time of the chosen procedure(s), may be used to display a single tooth, a plurality of teeth, a single jaw, or an entire bite set, may be displayed at any number of different viewing angles, and may be used for any applicable treatment step described herein, and each window may be used for viewing only purposes or for editing purposes.

Referring still to FIG. 8, in one embodiment of the present disclosure, individual tooth positions may be modified in window 803. Window 803 may allow for the user or treating professional to display individual teeth, a plurality of teeth, or an entire jaw. Teeth position modifications made in window 803 may be displayed in both windows 801 and 802. The polymeric shell appliance system is one method for treating the position and geometry of individual teeth, and as such, modifications in individual tooth positions is incorporated into the polymeric shell appliance system part of the overall procedure, and therefore does effect the manufacturing process of the polymeric shell appliances. Additionally, since window 802 displays both the target results after the polymeric shell appliance system process and a supplementary procedure, changes made to individual tooth positions also is displayed in window 802. Since changes in the individual tooth positions may affect the scope of the supplementary orthodontic procedure, the data set indicating the changes in terms of millimeters, degrees, and direction of change is updated.

Still referring to FIG. 8, in yet another embodiment of the present disclosure, when the position of the upper or lower or both arches of a patient are positioned by the treating professional in window 803, the changes are not applied to the target result tooth parameters shown in window 801. This implies that the polymeric shell appliances are designed for manufacture without taking into account this change. However, the change would appear in window 802 as a result of a supplementary orthodontic treatment process. This is due to the fact that changing positions of the arches of a patient may lower the efficiency of the polymeric shell appliances system process, and therefore may it may be preferable to treat such conditions through the use of a supplementary procedure, such as oral surgery. The change in position of the upper or lower or both jaws depicted in window 802 in relation to the target result depicted in window 801 may be displayed as a data set including, among others, changes in terms of millimeters, degrees, and direction of change. This allows for accurate determination of the scope of the surgical or other supplementary procedure to be applied to the patient's teeth.

The software program product and methods depicted in FIGS. 7-8 and described above may be applied as a new software program product, or as a feature or update to the existing ClinCheck® software, a part of the Invisalign® System by Align Technology, Inc., or as a feature or update to any other comparable existing software program product or system.

Figure 9:
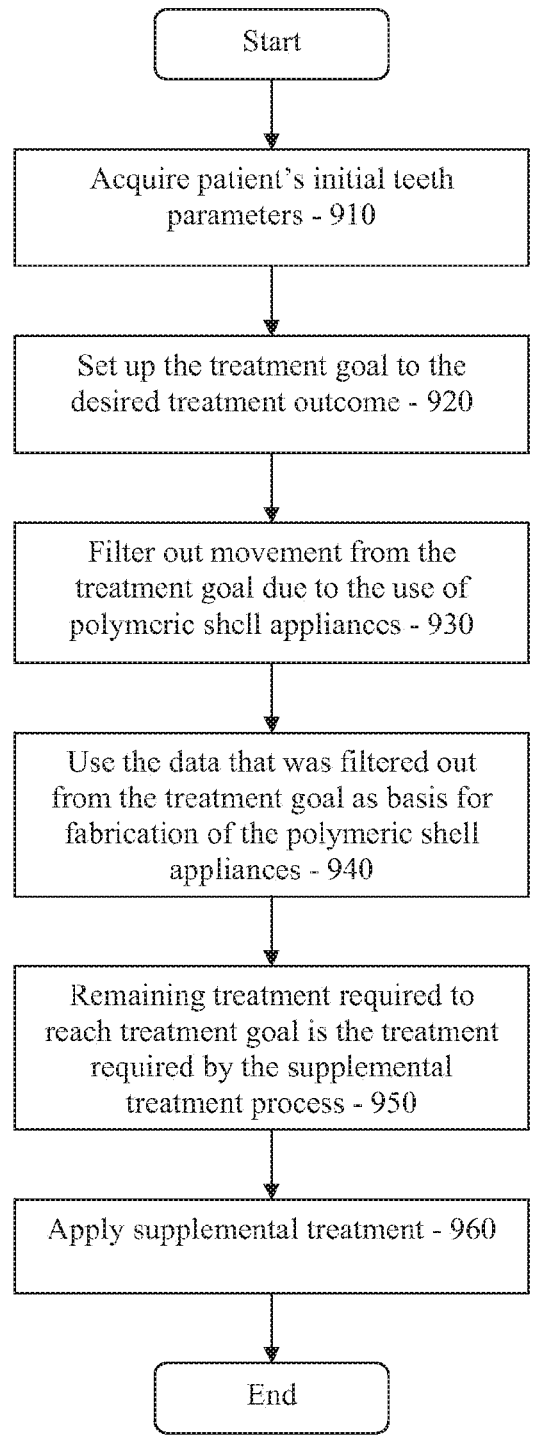
FIG. 9 illustrates a process for using multiple treatment types for orthodontic treatment in another aspect.

FIG. 9 illustrates a process for using multiple treatment types for orthodontic treatment in another aspect. Referring to the FIG. 9, after acquiring the patient's initial teeth parameters (910), the desired treatment goal is setup to the desired treatment outcome (920). Thereafter, movement from the treatment goal resulting from the use of polymeric shell appliances is filtered out (930), and the filtered data set is used as the basis for the fabrication process for the fabrication of the polymeric shell appliances (940). Referring again to FIG. 9, one or more supplemental treatment process (which may be different from the treatment base on the polymeric shell appliances) is determined for the remaining treatment necessary to reach the treatment goal (950), and thereafter, the supplementary treatment is applied for patient treatment (960).

Figure 10:
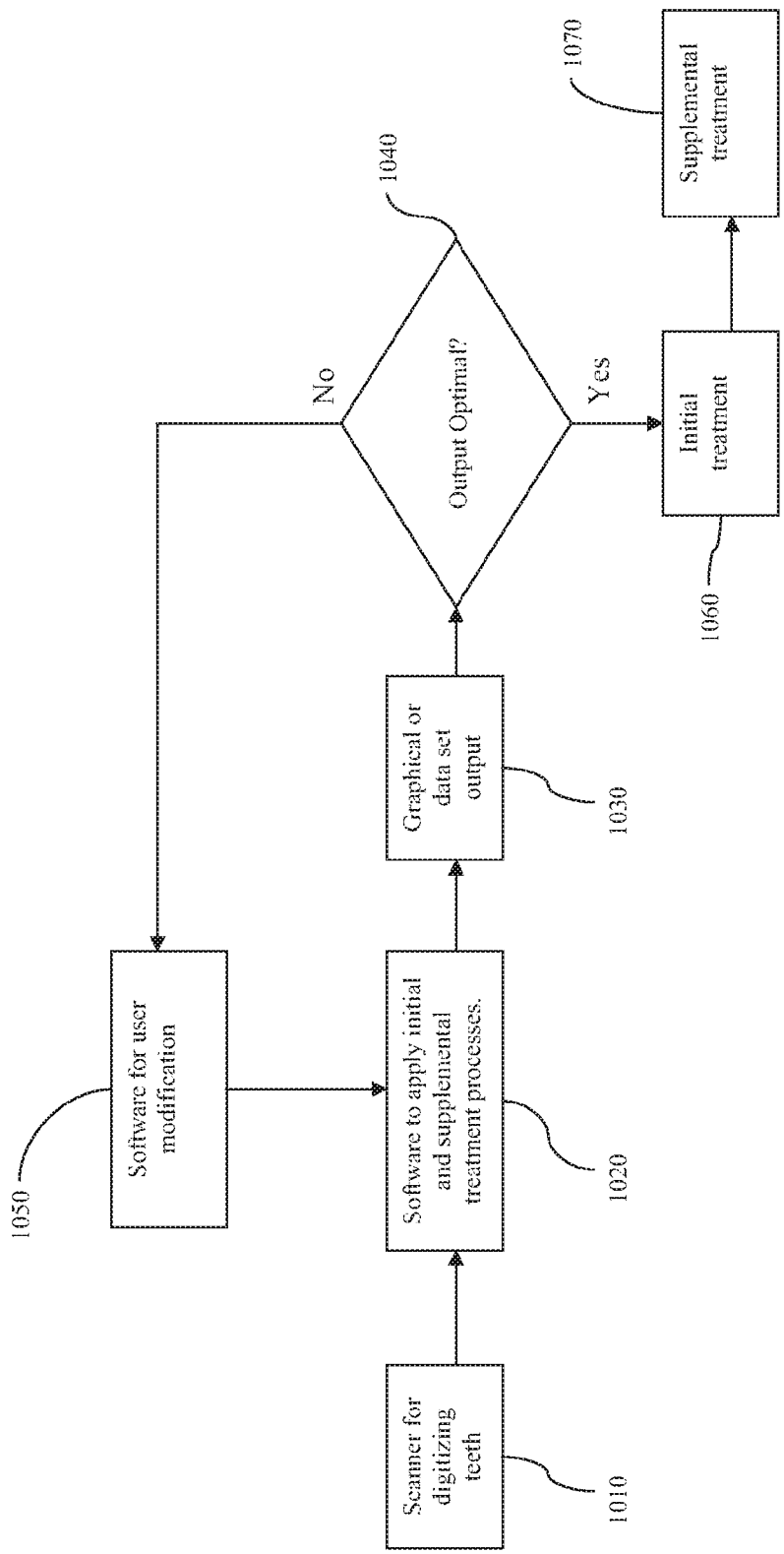
FIG. 10 illustrates a system for applying two treatment procedures for treating malocclusion of a patient's teeth.

FIG. 10 illustrates a general system for applying two treatment procedures for treating malocclusion of a patient's teeth. Referring to FIG. 10, in order to simulate treatment of a patient's teeth, a digital scan of the initial tooth parameters of the patient's teeth is needed. This may be achieved by the use of a scanner (1010), which may be of the type including, but not limited to, X-ray or MRI. The digital initial tooth parameters are loaded into a software program product (1020), which applies chosen initial and supplementary treatment processes to the initial teeth parameters.

The software program product may be configured to simulate the effects of the chosen treatment processes, and outputs the target results. The output may be displayed as either a graphical representation or a data set or a combination thereof (1030). The treating dental professional may inspect the output of the target results, which, in one embodiment of the present disclosure, is a display of both the results from the chosen initial treatment process only and the initial treatment process in conjunction with the supplementary treatment process, and decide if the output is an optimal occlusion (1040), or positioning of the teeth. In the case that the output is not of optimal result, the treating professional may edit the desired results (1050) and feed the new data back into the software program (1020) to update the simulation. Again, the results are displayed (1030) for the treating professional's review, and if necessary, more alterations are made (1050).

Once the treating professional is satisfied with the results of the simulation, the initial treatment procedure begins (1060). This may include, among others, the fabrication of a plurality of polymeric shell appliances based on the software program's data sets as described in FIGS. 5-6 above, the fabrication of other removable orthodontic appliances, the installation of a fixed bracket and arch wire orthodontic system, such as braces, or an oral surgery. At a pre-determined point before, during, or after the initial treatment procedure, a supplementary treatment procedure is implemented (1070). This may also include, among others, the fabrication of a plurality of polymeric shell appliances based on the software program's data sets as described in FIGS. 5-6 above, the fabrication of other removable orthodontic appliances, the installation of a fixed bracket and arch wire orthodontic system, such as braces, or an oral surgery. At the conclusion of the implementation of the shown system and methods incorporated therein, the target occlusion of the patient's teeth will be at the previously outputted results (1030) calculated and shown by the simulation (1020).

While the above methods and systems describe embodiments of various processes of an initial polymeric shell appliance system procedure being followed by a single supplementary orthodontic procedure, it is noted that any number of supplementary orthodontic procedures may be used. It is also noted that the supplementary orthodontic procedure may be performed before, during, or after the polymeric shell appliance system procedure and displays of each step in the overall process may be shown in the software program.

It is also noted that although a polymeric shell appliance system procedure is the described as one method of initial treatment, any number of other methods, including, but not limited to, fixed orthodontic appliances, such as braces, elastics or other removable appliances, treatments based on palate expansion, use of Class II or Class III appliances, and oral surgery may be the initial treatment method, and among others, polymeric shell appliance system procedures may be used as the supplementary orthodontic treatment procedure. In other words, any combination of orthodontic treatment procedures used to obtain an optimal target patient occlusion or combination of treatment procedures desired by the patient or treating dental professional are included within the scope of the present disclosure. For example, the one or more treatment processes may include the use of polymeric shell aligners using, for example, Invisalign® orthodontic appliances described in further detail in U.S. Pat. No. 5,975,893, the disclosure of which is incorporated by reference for all purposes, in conjunction with one or more other treatment processes discussed above.

In one embodiment of the present disclosure, there is provided positioning the teeth of a patient through the use of polymeric shell aligners in conjunction with a supplementary orthodontic treatment process. With the aid of virtual orthodontics software, two or more proposed treatment goals may be determined. The first of the treatment goals is the aligner treatment goal, or the result of the aligner treatment portion of the orthodontic process being applied to the initial teeth parameters. This treatment goal may be used as the basis for the manufacturing of the polymeric shell aligner appliances. The second or more treatment goals may be configured to reflect the target result after simulations of the supplemental treatment procedures are applied to the post-aligner treatment teeth parameters.

In another aspect, there is provided method and system to effectively simulate more than one proposed treatment goal, while maintaining the Invisalign® based treatment system portion of the treatment separate for fabrication purposes. In this manner, a display output may be provided that illustrate both the target results from the Invisalign® based treatment process, or other treatment process or system, and the results from the supplementary treatment process, and a data set accurately comparing the two results.

Accordingly, a method in one aspect includes receiving digital representations of the initial parameters of a dentition, simulating a first orthodontic treatment process on the digital representations of the initial parameters, displaying a set of output results from the simulation of the first orthodontic treatment process, simulating a second orthodontic treatment process on the output results from the simulation of the first orthodontic treatment process, and displaying a set of output results from the simulation of the second orthodontic treatment process.

In one aspect, the method may include a fabrication process to process one or more orthodontic appliances based at least in part on the output results from the first or second orthodontic processes.

The first orthodontic treatment process may include a polymeric shell appliances system treatment process.

In a further aspect, the second orthodontic treatment process may include a polymeric shell appliances system treatment process.

Further, the fabrication process may include fabricating a plurality of polymeric shell appliances based on the simulation of the first orthodontic treatment process.

Also, the fabrication process may include fabricating a plurality of polymeric shell appliances based on the simulation of the second orthodontic treatment process.

The method in yet another aspect may include modifying the first or second orthodontic treatments before manufacturing one or more orthodontic appliances based at least in part on one or more of the first or second orthodontic treatment processes.

In still another aspect, the method may include displaying the set of output results from the simulation of the first orthodontic treatment process and the set of output results from the simulation of the second orthodontic treatment process simultaneously.

Additionally, the method may include displaying a data set of information for use in the second orthodontic treatment in reference to the output results of the first orthodontic treatment.

Moreover, the first orthodontic treatment process may be different than the second orthodontic treatment process, or alternatively, the first orthodontic treatment process may be the same as the second orthodontic treatment process.

In yet a further aspect, an end point of one of the first orthodontic treatment process or the second orthodontic treatment process may substantially coincide with a beginning point of the other one of the first orthodontic treatment process or the second orthodontic treatment process. That is, in one aspect, the end point or conclusion of one of the first or second orthodontic treatment process may define or coincide with the beginning or the starting point of the other one of the first or second orthodontic treatment process.

The first orthodontic treatment process and the second orthodontic treatment process may include one or more of a palate expansion treatment, a Class II appliance based treatment, a Class II appliance based treatment, a polymeric shell appliance based treatment, a wire and bracket based treatment, or one or more combinations thereof.

A computer program product in accordance with one embodiment may include a medium readable by a computer, the computer readable medium having computer program code adapted to: receive digital representations of the initial parameters of a dentition, simulate a first orthodontic treatment process on the digital representations of the initial parameters, display a set of output results from the simulation of the first orthodontic treatment process, simulate a second orthodontic treatment process on the output results from the simulation of the first orthodontic treatment process, and display a set of output results from the simulation of the second orthodontic treatment process.

In one embodiment, the medium readable by the computer, the computer readable medium having computer program code may be adapted to perform a fabrication process to process one or more orthodontic appliances based at least in part on the output results from the first or second orthodontic processes.

Additionally, the medium readable by the computer, the computer readable medium having computer program code may be adapted to modify the first or second orthodontic treatments before manufacturing one or more orthodontic appliances based at least in part on one or more of the first or second orthodontic treatment processes.

In still another aspect, the medium readable by the computer, the computer readable medium having computer program code may be adapted to display the set of output results from the simulation of the first orthodontic treatment process and the set of output results from the simulation of the second orthodontic treatment process simultaneously.

Still in a further aspect, the medium readable by the computer, the computer readable medium having computer program code may be adapted to display a data set of information for use in the second orthodontic treatment in reference to the output results of the first orthodontic treatment.

Various other modifications and alterations in the structure and method of operation of the present disclosure will be apparent to those skilled in the art without departing from the scope and spirit of the present disclosure. Although the embodiments of the present disclosure has been described in connection with specific embodiments, it should be understood that the embodiments as claimed should not be unduly limited to such specific embodiments. It is intended that the following claims define the scope of the present disclosure and that structures and methods within the scope of these claims and their equivalents be covered thereby.

What is claimed is:

1. A method for creating a visualization of results corresponding to a dental treatment, said method comprising:
   receiving digital representations of initial teeth parameters of a dentition;
   identifying a desired target occlusion for the dentition;
   simulating a first orthodontic treatment process on the digital representations of the initial teeth parameters to produce a first set of output results;
   simulating a second orthodontic treatment process on the first set of output results from the simulation of the first orthodontic treatment process to produce a second set of output results, the first set of output results from the simulation of the first orthodontic treatment process comprising supplementary teeth parameters;
   iteratively altering the first orthodontic treatment process and the second orthodontic treatment process until the second set of output results becomes compatible with the desired target occlusion; and
   simultaneously displaying the simulation of the first orthodontic treatment process and the simulation of the second orthodontic treatment process.

2. The method of claim 1, wherein the simulating the first orthodontic treatment process comprises:
   virtually applying a first chosen treatment to the initial teeth parameters of the dentition.

3. The method of claim 2, wherein the simulating the second orthodontic treatment process comprises:
   virtually applying a second chosen treatment to the supplementary teeth parameters, wherein the first chosen treatment is a different treatment type than the second chosen treatment.

4. The method of claim 3, further comprising simulating a third orthodontic treatment process on the second set of output results, wherein simulating the third orthodontic treatment process comprises:
   virtually applying a third chosen treatment to the supplementary teeth parameters, wherein the first chosen treatment is a different treatment type than the second chosen treatment and the third chosen treatment.

5. The method of claim 1, further comprising:
   utilizing a polymeric shell appliance system treatment process for the first orthodontic treatment process; and
   utilizing the polymeric shell appliance system treatment process for the second orthodontic treatment process.

6. The method of claim 1, further comprising:
   fabricating one or more orthodontic appliances based at least in part on the first set of output results from the first orthodontic treatment process.

7. The method of claim 1, further comprising:
   displaying a data set of information for use in the second orthodontic treatment process in reference to the first set of output results of the first orthodontic treatment process.

8. The method of claim 1, wherein the first orthodontic treatment process and the second orthodontic treatment process includes one or more of a palate expansion treatment, a Class II appliance based treatment, a Class III appliance based treatment, a polymeric shell appliance based treatment, a wire and bracket based treatment, or one or more combinations thereof.

9. A non-transitory computer readable storage medium having stored thereon, computer-executable instructions that, when executed by a computer, cause the computer to perform a method comprising:
   receiving digital representations of initial teeth parameters of a dentition;
   identifying a desired target occlusion for the dentition;
   simulating a first orthodontic treatment process on the digital representations of the initial teeth parameters to produce a first set of output results;
   simulating a second orthodontic treatment process on the first set of output results from the simulation of the first orthodontic treatment process to produce a second set of output results, the first set of output results from the simulation of the first orthodontic treatment process comprising supplementary initial teeth parameters;
   iteratively altering the first orthodontic treatment process and the second orthodontic treatment process until the second set of output results becomes compatible with the desired target occlusion; and
   simultaneously displaying the simulation of the first orthodontic treatment process and the simulation of the second orthodontic treatment process.

10. The non-transitory computer readable storage medium of claim 9, wherein the simulating the first orthodontic treatment process comprises:
    virtually applying a first chosen treatment to the initial teeth parameters of the dentition.

11. The non-transitory computer readable storage medium of claim 10, wherein the simulating the second orthodontic treatment process comprises:
    virtually applying a second chosen treatment to the supplementary teeth parameters, wherein the first chosen treatment is a different treatment type than the second chosen treatment.

12. The non-transitory computer readable storage medium of claim 11, wherein the method comprises:

simulating a third orthodontic treatment process on the second set of output results, wherein simulating the third orthodontic treatment process comprises virtually applying the third orthodontic treatment process to the supplementary teeth parameters, wherein the first orthodontic treatment process is a different treatment type than the second orthodontic treatment process and the third orthodontic treatment process.

13. The non-transitory computer readable storage medium of claim 9, further comprising:
instructions to utilize a polymeric shell appliance system treatment process for the first orthodontic treatment process; and
instructions to utilize the polymeric shell appliance system treatment process for the second orthodontic treatment process.

14. The non-transitory computer readable storage medium of claim 9, further comprising:
instructions to base a fabrication process for one or more orthodontic appliances at least in part on the first or second set of output results from the first orthodontic treatment process.

15. The non-transitory computer readable storage medium of claim 9, further comprising:
instructions to display a data set of information for use in the second orthodontic treatment process in reference to the first or second set of output results of the first orthodontic treatment process.

16. The non-transitory computer readable storage medium of claim 9, wherein each of the first orthodontic treatment process and the second orthodontic treatment process includes one or more of a palate expansion treatment, a Class II appliance based treatment, a Class III appliance based treatment, a polymeric shell appliance based treatment, a wire and bracket based treatment, or one or more combinations thereof.

17. A method for creating a visualization of results corresponding to a dental treatment, said method comprising:
receiving digital representations of initial teeth parameters of a dentition;
identifying a desired target occlusion for the dentition;
simulating a first orthodontic treatment process on the digital representations of the initial teeth parameters to produce a first set of output results,
the simulating the first orthodontic treatment process comprises:
virtually applying a first chosen treatment to the initial teeth parameters of the dentition;
simulating a second orthodontic treatment process on the first set of output results from the simulation of the first orthodontic treatment process to produce a second set of output results, wherein:
the first set of output results from the simulation of the first orthodontic treatment process comprises supplementary initial teeth parameters, and
the simulating the second orthodontic treatment process comprises:
virtually applying a second chosen treatment to the supplementary initial teeth parameters, the first chosen treatment being a different treatment type than the second chosen treatment;
iteratively altering the first orthodontic treatment process and the second orthodontic treatment process until the second set of output results becomes compatible with the desired target occlusion; and
simultaneously displaying the simulation of the first orthodontic treatment process and the second orthodontic treatment process.

18. The method of claim 17, further comprising:
utilizing a polymeric shell appliance system treatment process for the first orthodontic treatment process; and
utilizing the polymeric shell appliance system treatment process for the second orthodontic treatment process.

19. The method of claim 17, further comprising:
displaying a data set of information for use in the second orthodontic treatment process in reference to the first set of output results of the first orthodontic treatment process.

20. The method of claim 17, wherein the first orthodontic treatment process and the second orthodontic treatment process includes one or more of a palate expansion treatment, a Class II appliance based treatment, a Class III appliance based treatment, a polymeric shell appliance based treatment, a wire and bracket based treatment, or one or more combinations thereof.

* * * * *